US006682721B2

(12) United States Patent
Kim et al.

(10) Patent No.: US 6,682,721 B2
(45) Date of Patent: *Jan. 27, 2004

(54) PATCHES FOR TEETH WHITENING

(75) Inventors: Ji-Young Kim, Daejeon (KR); Jong-Ho Kim, Daejeon (KR); Sug-Youn Chang, Daejeon (KR); Sei-Young Yun, Seoul (KR)

(73) Assignee: LG Household & Healthcare Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 10/049,817

(22) PCT Filed: Feb. 13, 2001

(86) PCT No.: PCT/KR01/00207

§ 371 (c)(1),
(2), (4) Date: Feb. 19, 2002

(87) PCT Pub. No.: WO01/68045

PCT Pub. Date: Sep. 20, 2001

(65) Prior Publication Data

US 2003/0082114 A1 May 1, 2003

(30) Foreign Application Priority Data

Mar. 17, 2000 (KR) ......................... 2000-13636
Dec. 8, 2000 (KR) ......................... 2000-74599

(51) Int. Cl.$^7$ ................................. A61K 7/20
(52) U.S. Cl. .................... 424/53; 424/448; 424/449
(58) Field of Search ................... 424/49–58, 448, 424/449

(56) References Cited

U.S. PATENT DOCUMENTS

| 4,517,173 A | 5/1985 | Kizawa et al. |
| 4,696,757 A | 9/1987 | Blank et al. |
| 4,713,243 A | 12/1987 | Schiraldi et al. |
| 4,728,291 A | 3/1988 | Golub |
| 4,741,700 A | 5/1988 | Barabe |
| 4,741,941 A | 5/1988 | Englebert |
| 4,786,253 A | 11/1988 | Morais |
| 4,799,888 A | 1/1989 | Golub |
| 4,812,308 A | 3/1989 | Winston |
| 4,839,156 A | 6/1989 | Ng |
| 4,839,157 A | 6/1989 | Mei-King |
| RE33,093 E | 10/1989 | Schiraldi et al. |
| 4,891,211 A | 1/1990 | Winston |
| 4,895,721 A | 1/1990 | Drucker |
| 4,900,552 A * | 2/1990 | Sanvordeker et al. ....... 424/422 |
| 4,900,554 A | 2/1990 | Yanagibashi |
| 4,919,615 A | 4/1990 | Croll |
| 4,933,182 A | 6/1990 | Higashi et al. |
| 4,983,379 A | 1/1991 | Schaeffer |
| 4,983,380 A | 1/1991 | Yarborough |
| 5,000,940 A | 3/1991 | Staples |
| 5,008,106 A | 4/1991 | Merianos |
| 5,009,885 A | 4/1991 | Yarborough |
| 5,032,178 A | 7/1991 | Cornell |
| 5,041,280 A | 8/1991 | Smigel |
| 5,055,287 A | 10/1991 | Kessler |
| 5,059,417 A | 10/1991 | Williams |
| 5,084,268 A | 1/1992 | Thaler |
| 5,098,303 A | 3/1992 | Fischer |
| 5,110,583 A | 5/1992 | Sampathkumar |
| 5,122,365 A | 6/1992 | Murayama |
| 5,128,122 A | 7/1992 | Cerami |
| 5,130,124 A | 7/1992 | Merianos |
| 5,166,233 A | 11/1992 | Kuroya |
| 5,171,564 A | 12/1992 | Nathoo et al. |
| RE34,196 E | 3/1993 | Munro |
| 5,192,532 A | 3/1993 | Guay |
| 5,208,010 A | 5/1993 | Thaler |
| 5,217,710 A | 6/1993 | Williams |
| 5,234,342 A | 8/1993 | Fischer |
| 5,234,957 A | 8/1993 | Mantelle |
| 5,240,415 A | 8/1993 | Haynie |
| 5,256,402 A | 10/1993 | Prencipe et al. |
| 5,279,816 A | 1/1994 | Church |
| 5,281,412 A | 1/1994 | Lukacovic |
| 5,290,566 A | 3/1994 | Schow |
| 5,292,502 A | 3/1994 | Burke et al. |
| 5,302,375 A | 4/1994 | Viscio |
| 5,310,563 A | 5/1994 | Curtis et al. ................ 339/74 |
| 5,326,685 A | 7/1994 | Gaglio |
| 5,332,576 A | 7/1994 | Mantelle |
| 5,340,314 A | 8/1994 | Tarvis |

(List continued on next page.)

FOREIGN PATENT DOCUMENTS

| GB | 2108841 | 5/1983 |
| JP | 10017448 | 1/1998 |
| JP | 2000-281548 | 10/2000 |
| WO | WO 98/55044 | 3/1999 |
| WO | WO 99/62472 | 12/1999 |
| WO | 99/62472 | * 12/1999 |
| WO | WO 00/54699 | 9/2000 |
| WO | WO 01168045 | 9/2001 |

OTHER PUBLICATIONS

U.S. patent application No. 10/445,589 filed May 27, 2003 (and Preliminary Amendment) filed May 27, 2003 entitled Patches for Whitening Teeth; 41 pp.

Primary Examiner—Shep Rose
(74) Attorney, Agent, or Firm—Fox Rothschild LLP

(57) ABSTRACT

The present invention relates to a dry type tooth whitening patch comprising peroxide as a tooth whitening agent. In particular, disclosed is a dry type tooth whitening patch in which a peroxide is contained, as a teeth whitening agent, in a matrix type adhesive layer. The adhesive layer includes, as a base polymer thereof, a hydrophilic glass polymer which provides a strong adhesion to teeth while releasing the tooth whitening agent when hydrated on the enamel layers of teeth in the moist oral cavity. The dry type patch according to the present invention is convenient in use, as compared to wet type patches. Further, it exhibits a superior adhesion while being maintained in a state attached to the teeth for a lengthened period of time so as to assure an enough contact time between the whitening agent in the patch and stains on the teeth, thereby giving a sufficient whitening effect.

4 Claims, No Drawings

U.S. PATENT DOCUMENTS

| | | | |
|---|---|---|---|
| 5,340,581 A | 8/1994 | Tseng | |
| 5,348,734 A | 9/1994 | Ratcliff | |
| 5,366,285 A | 11/1994 | Borgen et al. | |
| 5,372,802 A | 12/1994 | Barrows | |
| 5,376,006 A | 12/1994 | Fischer | |
| 5,380,198 A | 1/1995 | Suhonen | |
| 5,401,495 A | 3/1995 | Murayama | |
| 5,409,631 A | 4/1995 | Fischer | |
| 5,425,953 A | 6/1995 | Sintov | |
| 5,437,858 A | 8/1995 | Hungerbach | |
| 5,438,076 A | 8/1995 | Friedman | |
| 5,505,956 A * | 4/1996 | Kim et al. | 424/448 |
| 5,536,285 A | 7/1996 | Isaksson et al. | |
| 5,560,379 A | 10/1996 | Pieczenik | |
| 5,565,190 A | 10/1996 | Santalucia | |
| 5,575,654 A | 11/1996 | Fontenot | |
| 5,611,687 A | 3/1997 | Wagner | |
| 5,614,174 A | 3/1997 | Hsu | |
| 5,620,322 A | 4/1997 | Lococo | |
| 5,626,866 A | 5/1997 | Ebert | |
| 5,631,000 A | 5/1997 | Pellico | |
| 5,631,055 A | 5/1997 | Vines | |
| 5,639,445 A | 6/1997 | Curtis et al. | 339/14 |
| 5,648,064 A | 7/1997 | Gaffar | |
| 5,683,680 A | 11/1997 | Santalucia | |
| 5,689,182 A | 11/1997 | Togo | |
| 5,700,478 A * | 12/1997 | Biegajski et al. | 424/434 |
| 5,707,611 A | 1/1998 | Ikemura | |
| 5,707,736 A | 1/1998 | Levy | |
| 5,713,738 A | 2/1998 | Yarborough | |
| 5,718,886 A | 2/1998 | Pellico | |
| 5,723,132 A | 3/1998 | Tseng | |
| 5,725,843 A | 3/1998 | Fischer | |
| 5,746,598 A | 5/1998 | Fischer | |
| 5,766,574 A | 6/1998 | Christina-Beck | |
| 5,770,105 A | 6/1998 | Fischer | |
| 5,770,182 A | 6/1998 | Fischer | |
| 5,776,437 A | 7/1998 | Burgess | |
| 5,785,527 A | 7/1998 | Jensen | |
| 5,785,957 A | 7/1998 | Losee | |
| 5,814,303 A | 9/1998 | Williams | |
| 5,814,304 A | 9/1998 | Wong et al. | |
| 5,820,822 A | 10/1998 | Kross | |
| 5,820,852 A | 10/1998 | Burgess | |
| 5,820,854 A | 10/1998 | Glandorf | |
| 5,846,570 A | 12/1998 | Barrow | |
| 5,849,269 A | 12/1998 | Burgess | |
| 5,851,514 A | 12/1998 | Hassan | |
| 5,855,875 A | 1/1999 | Williams | |
| 5,858,332 A | 1/1999 | Jensen | |
| 5,863,202 A | 1/1999 | Fontenot et al. | |
| 5,879,691 A | 3/1999 | Sagel et al. | 439/102 |
| 5,885,553 A | 3/1999 | Michael | |
| 5,885,554 A | 3/1999 | Michael | |
| 5,891,453 A * | 4/1999 | Sagel et al. | 424/53 |
| 5,894,017 A | 4/1999 | Sagel et al. | |
| 5,902,568 A | 5/1999 | Ryles | |
| 5,908,614 A | 6/1999 | Montgomery | |
| 5,914,118 A * | 6/1999 | Yamamura et al. | 424/402 |
| 5,915,969 A | 6/1999 | Linden | |
| 5,922,307 A | 7/1999 | Montgomery | |
| 5,928,628 A | 7/1999 | Pellico | |
| 5,932,193 A | 8/1999 | Lopez | |
| 5,945,032 A | 8/1999 | Breitenbach | |
| 5,980,249 A | 11/1999 | Fontenot | |
| 5,985,249 A | 11/1999 | Fischer | |
| 5,989,569 A | 11/1999 | Dirksing et al. | 439/102 |
| 6,007,795 A | 12/1999 | Masterman | |
| 6,017,515 A | 1/2000 | van den Bosch | |
| 6,022,528 A | 2/2000 | Waterfield | |
| 6,030,222 A | 2/2000 | Tarver | |
| 6,036,493 A | 3/2000 | Sharma | |
| 6,036,943 A | 3/2000 | Fischer | |
| 6,045,811 A | 4/2000 | Dirksing et al. | |
| 6,072,100 A * | 6/2000 | Mooney et al. | 424/448 |
| 6,080,811 A * | 6/2000 | Schehlmann et al. | 433/229 |
| 6,083,421 A | 7/2000 | Huang | |
| 6,086,855 A | 7/2000 | Fischer | |
| 6,096,328 A | 8/2000 | Sagel et al. | |
| 6,106,293 A | 8/2000 | Wiesel | |
| 6,110,446 A | 8/2000 | Prencipe | |
| 6,121,213 A | 9/2000 | Vergara | |
| 6,136,297 A | 10/2000 | Sagel et al. | |
| 6,149,895 A | 11/2000 | Kutsch | |
| 6,155,832 A | 12/2000 | Wiesel | |
| 6,174,516 B1 | 1/2001 | Curtis | |
| 6,190,689 B1 * | 2/2001 | Hoffmann et al. | 424/448 |
| 6,197,331 B1 * | 3/2001 | Lerner et al. | 424/448 |
| 6,221,341 B1 | 4/2001 | Montgomery | |
| 6,241,973 B1 | 6/2001 | Rinne | |
| 6,274,122 B1 | 8/2001 | McLaughlin | |
| 6,277,458 B1 | 8/2001 | Dirksing et al. | |
| 6,280,708 B1 | 8/2001 | Ryles | |
| 6,284,152 B1 | 9/2001 | Kross | |
| 6,290,934 B1 | 9/2001 | Kramer | |
| 6,290,935 B1 | 9/2001 | Masters | |
| 6,306,370 B1 | 10/2001 | Jensen | |
| 6,309,622 B1 | 10/2001 | Watkings | |
| 6,309,625 B1 | 10/2001 | Jensen | |
| 6,312,666 B1 | 11/2001 | Oxman | |
| 6,312,670 B1 | 11/2001 | Montgomery | |
| 6,312,671 B1 | 11/2001 | Jensen | |
| 6,319,510 B1 * | 11/2001 | Yates | 424/443 |
| 6,322,773 B1 | 11/2001 | Montgomery | |
| 6,322,774 B1 | 11/2001 | Jensen | |
| 6,325,997 B1 | 12/2001 | Christopfel | |
| 6,331,291 B1 | 12/2001 | Glace | |
| 6,331,292 B1 | 12/2001 | Montgomery | |
| 6,342,206 B1 | 1/2002 | Gopalkrishnan | |
| 6,348,187 B1 | 2/2002 | Pan | |
| 6,350,437 B1 | 2/2002 | Pasetti | |
| 6,350,438 B1 | 2/2002 | Witt | |
| 6,365,134 B1 | 4/2002 | Orlowski | |
| 6,368,576 B1 | 4/2002 | Jensen | |
| 6,375,933 B1 | 4/2002 | Subramanyam | |
| 6,379,653 B1 | 4/2002 | Aaslyng | |
| 6,391,283 B1 | 5/2002 | Jensen | |
| 6,391,286 B1 | 5/2002 | Mitra | |
| 6,403,060 B1 | 6/2002 | Bornstein | |
| 6,409,992 B1 | 6/2002 | Kleinberg | |
| 6,409,993 B1 | 6/2002 | Jensen | |
| 6,409,994 B1 | 6/2002 | Dahlin | |
| 6,413,502 B1 | 7/2002 | Bornstein | |
| 6,419,902 B1 | 7/2002 | Wright | |
| 6,419,905 B1 | 7/2002 | Alvarez Hernandez | |
| 6,419,906 B1 | 7/2002 | Xu et al. | |
| 6,423,300 B1 | 7/2002 | Kleinberg | |
| 6,435,873 B1 * | 8/2002 | Burgio | 433/80 |
| 6,440,396 B1 | 8/2002 | McLaughlin | |
| 6,440,749 B1 | 8/2002 | Cerami | |
| 6,447,757 B1 | 9/2002 | Orlowski | |
| 6,457,469 B1 | 10/2002 | Mueller | |
| 6,458,340 B1 | 10/2002 | Ibsen | |
| 6,458,380 B1 * | 10/2002 | Leaderman | 424/49 |
| 6,471,947 B2 | 10/2002 | Bhakoo | |
| 6,475,472 B2 | 11/2002 | Joiner | |

| | | | |
|---|---|---|---|
| 6,479,037 B1 | 11/2002 Montgomery | 6,509,007 B2 | 1/2003 Rajaiah |
| 6,485,709 B2 | 11/2002 Banerjee | 6,514,483 B2 | 2/2003 Xu |
| 6,488,913 B2 | 12/2002 Orlowski | 6,514,484 B2 | 2/2003 Rajaiah |
| 6,488,914 B2 | 12/2002 Montgomery | 6,517,350 B2 * | 2/2003 Diasti et al. .................. 424/53 |
| 6,500,408 B2 * | 12/2002 Chen ........................... 424/53 | 2002/0081555 A1 | 6/2002 Wiesel |
| 6,503,485 B1 | 1/2003 Allred | | |
| 6,503,486 B2 | 1/2003 Xu | * cited by examiner | |

PATCHES FOR TEETH WHITENING

TECHNICAL FIELD

The present invention relates to a dry type patch that makes stains of teeth removed and teeth whitened only through attachment to the teeth. More particularly, it relates to a dry type patch comprising a hydrophilic glass polymer as an adhesive layer in a matrix type on a backing layer and peroxide as a whitening agent, in which the hydrophilic glass polymer provides a strong adhesive attachment to teeth while releasing tooth whitening agent when hydrated by the moist on teeth. The dry type patch of the present invention is characterized by having unobtrusive appearance since it is transparent. Therefore, it can be used without interfering with normal social life. In addition, the patch can be used conveniently since the stability with time of peroxides in the adhesive layer at a high temperature can be assured.

BACKGROUND ART

As people's interest in whitening teeth is increased, a number of toothpaste having tooth whitening effect is commercially available. However, even though the toothpaste contains a tooth whitening agent of good performance, it is hard to achieve a significant teeth whitening effect in a short period of time, by brushing teeth for 1 to 3 minutes of contact time between teeth and toothpaste.

Recently, in order to solve the above problems, a number of patent applications related thereto has been filed and tooth whitening products of various formulations have been introduced in the markets.

Among them, for the professional whitening gel, a patient needs to visit a dentist once or twice to examine his exact dental condition and to measure size of teeth. The dentist manufactures a mouth tray fitting teeth of the respective patient based on the examination and measurement. The patient applies a whitening gel to inner walls and a trough of the tray following instructions at home and wears the tray overnight or twice a day for 2 to 4 days in a week. Typically, the above treatment will be completed in 2 to 4 weeks. However, it has disadvantages in that using the tray is not convenient for a patient and when wearing the tray, the patient experiences discomfort feeling. Further, the patient has to pay lots of money to fabricate his own mouth tray. In addition, a peroxide gel at a high concentration loaded in the mouth tray may flow upon teeth and contact with gum, causing irritation or damage of the gum or mouth cavity.

In order to solve these problems, Japanese Patent No. 10,017,448, assigned to Lion Cor. discloses plasters for oral cavity, which comprises a teeth adhesion layer and a supporting layer. A whitening agent which can be used in this patent includes kojic acid and derivatives thereof, ascorbic acid and derivatives thereof, carbamide peroxide and the like but kojic acid and various salts thereof are described as being particularly effective. However, since the above-mentioned whitening agents have a strong acidity, it may cause irritation in an oral cavity due to a low pH. Such agents can provide superior whitening effect at a high acidity. Therefore, it is difficult to obtain a plaster of good whitening effect without irritation.

The kojic acid is widely used in skin care products. However, it has not been proved to have tooth-whitening effect and has not been used as a tooth-whitening agent. In practice, when adding ascorbic acid and derivatives thereof, or carbamide peroxide as a whitening agent respectively to a patch formulation comprising a glass polymer as an adhesive, discoloration and stickiness occurs as time goes by. In particular, when adding carbamide peroxide, severe problems occur in terms of storage as crystal forms at a temperature 40° C.

In addition, the whitening agents mentioned in the patent are usually considered to be unstable. However, the patent does not include a description with regarding to a stabilization of these whitening agents. The above patent seems to be an idea patent, which is formed by combining kojic acid, which is a typical raw material of cosmetic composition for skin whitening, produced by Lion Cor. into a plaster formulation using a common polymer without conducting concrete studies.

Japanese Patent No. 12,281,548, filed on Mar. 16, 1999 and published on May 30, 2000, discloses a tooth whitening kit set. Claim 2 describes a water-insoluble tape, sheet, film, dental tray, mouth tray, mouthpiece, impression pack, pack material, and chewing brushing having a plurality of protrusion on a surface contacting with teeth and prepared by forming upon dental arch. Upon reviewing the specification, the invention is characterized by thinly applying a whitening component in a gel phase on a supporting layer of the above appliances or by immersing the adhesion portion of the above appliances in a solution containing a whitening agent. That is, the appliances claimed in this patent are wet type. When using such type of appliances, the whitening agent may contact with hands or other part of body, causing irritation.

Further, the adhesion portion of water-insoluble tape or sheet is composed of woven or non-woven fabric, for example, rayon, cotton, silk or paper while the supporting layer is composed of water-insoluble film, for example, polyethylene, polypropylene, polyester, etc. Thus, it is not considered that the invention is improved over the Patent No. 10,017,448.

Meanwhile, this invention uses a poly phosphate as a whitening agent, instead of peroxide along with anionic surfactant and low molecular weight alcohol having not more than 3 of carbon atoms. It is described that the surfactant and low molecular weight alcohol are added to facilitate the condensed phosphate infiltrating into stains. However, though effectively infiltrating into stains, poly phosphate cannot remove intrinsic stain or heavy extrinsic stain.

U.S. Pat. Nos. 5,879,691, 5,891,453 and 5,989,569, and WO 98/55044, assigned to Procter & Gamble disclose a delivery system for a tooth whitener, comprising a transparent, thin and flexible polyethylene strip having a professional whitening gel and the like thereon, wherein the professional whitening gel and the like is pre-coated in a manufacturing process or applied directly by wearer before attaching the strip to teeth. Since it does not use a mouth tray, easiness to use is improved. Further, since the strip is thin and transparent, daily life is not interrupted when wearing the strip. However, upon reviewing the examples, it is noted that the invention of this patent is a wet type teeth-whitening system constructed by using a tooth whitening substance along with as a gelling agent, preferably carboxypolymethylene, obtained from B.F. Goodrich Company under trade name of Carbopol, water, pH adjusting agent and additive carrier materials and applying the substance onto a strip of flexible material. When handling this type of system or attaching and wearing the system onto teeth, the gel containing peroxide of a high concentration as a tooth whitener may adhere to and leave on hands, tongue, gum and the like. Therefore, there is room for improvement in handling. Further, since stabilization of peroxide in the formulation is not sufficiently assured, the whitening effect may be diminished when storing at a high temperature or for a long period of time.

WO 00/54699 discloses a strip improved in its shape over the strip of its parent patent so that a whitening agent and a strip contact with teeth in better fitting. The most important feature of this patent is that the strip is of a shape covering the user's front four teeth and two canine teeth while allowing the tips of the two canine teeth to protrude. When the strip covers the tips of the two canine teeth, it is difficult for the user to attach the strip conforming the contour of teeth so as to remain the bleaching gel in contact with the teeth surface for a sufficient time. However, when attaching a strip of a trapezoidal shape on the lower teeth and folding it over the teeth so as to attach it onto the backside of the teeth, the tongue may touch the strip, causing uncomfortable feeling. In order to improve a feeling of using the strip, it would be more desirable to provide an enough adhesion and flexibility for the system so that the system would be comfortably attached onto both the front side and the back side of the teeth than to assure a contact time by means of a shape of the system, without making the system in a trapezoidal shape or in a structure not covering the tips of two canine teeth.

U.S. Pat. Nos. 5,310,563 and 5,639,445, assigned to Colgate-Palmolive company, disclose a dental material comprising an active component dispersed in a polysiloxane polymer composition sold under the trade name Dow Corning 3179 Dilatant Compound by Dow Corning Corporation, which is attached to the teeth by pressing it against the teeth and the gum and easily removed from the teeth without breaking pieces and adhering to tooth surfaces. However, whereby the material has a construction with an active component capsulated in the polymer, the active component cannot be easily released. Consequently, it is required an extended contact time in order to obtain a tooth whitening effect.

DISCLOSURE OF THE INVENTION

It is an object of the present invention to provide a dry type patch for tooth whitening comprising a hydrophilic glass polymer as a material of an adhesive layer and a peroxide as a tooth whitening agent, which is capable of accomplishing a sufficient contact time between the tooth whitening agent and stains on surfaces of teeth. It is an other object of the present invention to provide a dry type patch for tooth whitening which is safe when a user handles by hands and fingers or while a user wears on teeth since the tooth whitening agent does not adhere to and leave on user's hands and not irritate sensitive skin in the moist oral cavity. It is a further object of the present invention to provide a dry type patch for tooth whitening, which can be used easily and conveniently and has a good wearing feeling, thereby comforting the user while wearing the patch.

A dry type patch for tooth whitening according to the present invention accomplishes the above and other objects.

The present invention provides a novel dry type patch for tooth whitening comprising peroxide as a tooth whitening agent. In particular, the present invention provides a dry type patch for tooth whitening in which peroxide is contained as a tooth whitening agent in an adhesive layer in a matrix type on a backing layer, which includes a hydrophilic glass polymer as a base polymer thereof. The hydrophilic glass polymer can provide a strong adhesion to teeth while releasing the tooth whitening agent dispersed therein when hydrated on the enamel layer of teeth in the moist oral cavity.

The dry type patch according to the present invention is convenient in use, as compared to a conventional wet type patch. Further, it exhibits a superior adhesion while being maintained in a state attached to the teeth for an extended period of time so as to assure an enough contact time between the tooth whitening agent in the patch and stains on the teeth, thereby giving sufficient tooth whitening effect.

For a dry type system for a tooth whitening, the stability with time of peroxide used as a tooth whitening agent raises an issue. In the present invention, in order to solve this problem, a stabilizer for peroxide is added. Further, by selecting a glass polymer having a good compatibility with peroxide and controlling appropriately the solvate ratio it is possible to solve the problem associated with the stability of peroxide even without adding a stabilizer. Therefore, according to the present invention, there is provided a novel dry type patch for tooth whitening, comprising a hydrophilic glass polymer as an adhesion layer of the patch and a peroxide as a tooth whitening agent dispersed therein and which attains to a stability of peroxide either by using a stabilizer for peroxide or by selecting a glass polymer having a good compatibility with peroxide and controlling the solvate ratio appropriately.

Also, according to the present invention, polyphosphates may be added along with peroxide as a tooth-whitening agent in order to enhance the tooth whitening effect.

In general, patches used in the medical purpose are divided into two categories: a wet type and a dry type. The wet type patch is for example, a hydrogel formulation, or a formulation formed by applying a gel to an adhesive layer or immersing an adhesive layer in a solution. This type of patch is characterized in that an initial state of the formulation is wet since content of water or humectant in the formulation is high. Meanwhile, the dry type is characterized in that an initial state of the formulation is dry since the content of water or humectant in the formulation is low. For delivering a moisturizer or other medicinal components to a dry skin, it is preferable to use the wet type of patches due to its good flexibility and watery property. However, the wet type patch formulation generally lacks adhesion strength. Further, since it is sticky from the initial state when a user handles it, a medicinal agent may adhere to hands when attaching the formulation onto a desired place. Moreover, in a certain case, a medicinal agent or a gel comprising a tooth whitening agent may pass through a supporting layer toward the opposite side thereof in accordance with formulation. Specially, for a patch formulation including peroxide at a high concentration applied in a gel containing a great quantity of humectant, when a user fumbles about to try to attach the patch fitting with contours of teeth, the peroxide may adhere to undesired site, such as hands, lip, tongue, etc, causing irritation. Further, the humectant usually has no taste. Therefore, if it leaves on tongue, the user may have an alien feeling.

Thus, the present inventors adopt the dry type for a new patch formulation. The dry type patch according to the present invention has advantages that it has a sufficient adhesion strength in the moist oral cavity while avoiding of a tooth whitening agent adhering to hands or other places as well as gum and tongue in the oral cavity and reducing an alien feeling.

In order to produce such a dry type patch, it is necessary to select a polymer, which is able to acquire an adhesion or strengthen its adhesion when hydrated by a small quantity of water at a desired place while having a little or no adhesion strength in a dry state. Also, the polymer should begin to release a tooth whitening agent via hydration. The inventors discovered that a hydrophilic glass polymer has such properties and thus forms the present invention by employing the hydrophilic glass polymer as a base polymer in an adhesive layer of a matrix type patch.

According to the present invention, as a backing layer a sheet formed by using water-insoluble and water-impermeable polymer as a film former is used. The backing layer plays a role of preventing the adhesive layer from adhering to gum or tongue and the patch from deforming or being detached from teeth by saliva.

The tooth whitening effect may be controlled by adjusting a thickness of patch or by varying tooth whitening agents. Since the present patch is transparent, it is possible for user to observe oxygen bubbles of peroxide bleaching teeth or removing stains during wearing the patch and thereby to recognize visibly a whitening effect. Also, since the patch of transparent material according to the present invention is not conspicuous upon wearing, the user's daily life would not be impeded.

The matrix type patch of the present invention is intended to be attached not to a skin or a mucous membrane, but to an enamel layer of tooth so as to supply a tooth whitening agent to surface of teeth for a sufficient time.

The principle that the patch may be adhered to teeth and a whitening agent contained in the matrix is released on the surface of teeth is described below.

In fields of drug delivery systems, there has been suggested an idea using moisture transpired from skin in a transdermal formulation so as to release a drug when a predetermined time passes after attachment for transdermal delivery of drug with time lag. More particularly, a barrier impermeable to drug is provided between drug reservoir and skin adhesion surface in a transdermal formulation. When the formulation is attached to skin, the barrier is gradually hydrated by moisture transpired from skin, whereby its permeability to drug is increased. In this case, a hydrophilic glass polymer may be used as material of the barrier.

Based on the above idea, the present invention is formed by using a hydrophilic glass polymer in an adhesive layer of matrix type patch so that the whitening agent is not released in a dry state when the user handles the patch to attach it onto teeth, but is released when the polymer is hydrated by moist on teeth. Most of such glass polymers, when hydrated, provide sufficient adhesion strength to remain the contact state with surface of teeth. Thus, according to the present invention, it is not needed to use an additional means or features for fixing the patch against teeth so as to attain sufficient contact time between the whitening agent and teeth, such as marginal adhesive layer to be folded onto back side of teeth. Also, the patch of the present invention does not generate significant irritation of gum or skin in oral cavity when it directly contacts with gum or the skin. In addition, the patch of the present invention can be attached to teeth only so that the whitening agent in not released onto gum. Thus, the first feature of the present invention is to use a hydrophilic glass polymer in the adhesive layer of the dry type patch.

For these purposes, a polymer which can be used in the adhesive layer of the patch according to the present invention includes poly alkyl vinyl ether-maleic acid copolymer (PVM/MA copolymer) such as, Gantrez AN 119, AN 139, and S-97, polyvinyl alcohol, polyacrylic acid, Poloxamer 407 (Pluronic), polyvinyl pyrrolidone-vinyl acetate copolymer (PVP/VA copolymer), such as Luviskol VA, and Plasdone S PVP/VA, polyvinyl pyrrolidone (PVP, K-15~K-120), Polyquaterium-11 (Gafquat 755N), Polyquaterium-39 (Merquat plus 3330), carbomer (Carbopol), hydroxy propyl methyl cellulose, hydroxy ethyl cellulose, hydroxy propyl cellulose, gelatin and alginate salt such as sodium alginate. The above-described polymers can be used alone or in a mixture. A solvent for these polymers includes water, ethanol or any mixture thereof.

The patch to be attached onto teeth should be flexible enough such that it is deformable to conform to contour line of teeth. Some polymers have a poor flexibility depending upon their classes. In this case, a suitable plasticizer may be added. Although such plasticizer may vary according to the class and preparation of the polymer used, propylene glycol, glycerin, and polyethylene glycol are generally usable.

The tooth whitening agent contained in the tooth enamel adhesive layer may be selected from a group consisting of hydrogen peroxide, carbamide peroxide, calcium peroxide, sodium percarbonate, sodium perborate, tetrasodium pyrophosphate peroxidate and mixtures thereof. Tetrasodium pyrophosphate peroxidate (TSPP-$H_2O_2$), which is an addition compound of tetrasodium pyrophosphate and hydrogen peroxide, displays properties of tetrasodium pyrophosphate, per se, as well as properties of hydrogen peroxide in state of an aqueous solution or crystal. Usually, tetrasodium pyrophosphate stabilizes hydrogen peroxide without changing intrinsic properties of hydrogen peroxide. In other words, it prevents a problem caused when using hydrogen peroxide alone. Decomposition of hydrogen peroxide may be promoted by metallic catalase, UV-ray, oxidase, thermal treatment, etc., whereas tetrasodium pyrophosphate peroxidate is stable against the above-described materials and treatments and displays intrinsic properties and functions of hydrogen peroxide. In practice, using tetrasodium pyrophosphate peroxidate in a liquid, gel or paste phase shows the good stability with time at a temperature of 40° C., as compared to using peroxide alone. However, even though using tetrasodium pyrophosphate peroxidate, the stability of peroxide in the patch cannot easily achieved.

In general, peroxide is known to be hardly stabilized in a product due to its good reactivity. Further, it has a poor compatibility with polymers. Stability of peroxide in a product relates to a type or preparation of the product. In connection with the stability of peroxide in a product, there are many patents dealing with the stabilization of peroxide in a ordinary gel, paste or solution phase and some of them are found to assure a stability of certain extent at a high temperature. However, there is no suggestion with respect to the stabilization of peroxide in a thin coated gel or patch. The present inventors likewise found after conducting much studies that such problem cannot be solved by means of known peroxide stabilizers. Now, the inventors have discovered a stabilizer, which can be used within range in application of the present invention without harming fundamental properties of the patch according to the present invention and can improve the stability with time of peroxide in the patch at a high temperature, during screening stabilizers for peroxide in the patch.

Therefore, in accordance with another aspects the present invention relates to the use of a stabilizer for peroxide along with a peroxide as a tooth whitening agent.

A stabilizer which has a good compatibility with peroxide comprises one or more selected from a group consisting of alkyl aryl sulphonate, alkyl sulphate, alkyl carboxylate, alkyl diphenyl oxide disulphonate, a series of Span, such as Span 60 (sorbitan stearate), Span 80 (sorbitan monooleate), Span 85 (sorbitan trioleate) and mixtures thereof. More detailed explanation will be described below.

According to the present invention, a peroxide is used as a main tooth-whitening agent in the patch. However, for the patch including only the whitening agent, content of peroxide in the patch decreases as time passes when stored the patch at a temperature of 40° C. Upon examining the whitening effect of the patch in vitro, it was observed that the whitening effect is lessened, compared to the initial stage. For a gel type formulation, loss of peroxide over a time is small even when an overdose of polymer is used, as a film forming agent and a special stabilizer for peroxide is not added. Even if formulation includes a peroxide which lacks a stability, a desired effect can be obtained by using a small amount of a chelating agent, such as EDTA or sodium citrate, commonly known as a stabilizer for a peroxide. However, in the present invention wherein a solvent of gel is vaporized to give a sheet-shaped patch, things are different. If a stabilizer is not used in the composition though the same as that used above, the stability with time of peroxide in the patch is more deteriorated than that obtained in a solution phase. Furthermore, upon addition of a chelating agent it is observed that a stability of peroxide in the patch dropped, compared before its addition. In addition, even when using a Dequest phosphonate class of a stabilizer, which is known for its superior stabilizing effect against a peroxide in the solution, satisfactory stabilization effect cannot be obtained.

As described above, the reason the stability with time of peroxide in the patch differs in accordance with formulation type such as a gel, liquid or sheet phase may be reflected in various way. According to U.S. Pat. No. 4,320,102, peroxide is characterized by being very sensitively decomposed through a catalytic reaction of by a minimal amount of metal contained in the composition. There have been reported data showing that where 0.1 mg of iron, 0.2 mg of copper, 0.1 mg of magnesium or 0.02 mg of chromium per 1 L of 5% peroxide aqueous solution, the peroxide would be decomposed. The present invention that is a sheet type patch formed by vaporization of solvent from a solution or gel phase should contain a high content of metal in the patch having a small thickness. Further, the sheet shaped patch has a wide surface area, which allows a high rate of reaction on the surface. In practice, it is found that gel applied thinly on a surface, leading a wide surface area, decreases in residual peroxide over the time pass, while gel including same composition, but contained in a container is stable at a relatively high temperature. For these reason, the patch such as the present invention requires some treatments or additives for stabilization of peroxides.

In the present invention, the stabilizer for peroxide used in the patch is composed of mainly surfactant or emulsifying agent, which forms micelles on the surface of sheet, causing a positive effect to the stabilization of peroxide. However, some of hydrophilic glass polymers, which can be used in the present invention, have a good compatibility with peroxide so that the peroxide can be sufficiently stabilized by adjusting solvent ratio without addition of certain stabilizer for peroxide. Thus, the present invention does not limited to essential inclusion of a stabilizer for peroxide.

Now, more detailed description is described below.

Hydrophilic glass polymers such as polyviny pyrrolidone (PVP, K-15~K-120), polyquaternium-11, polyquaternium-39, polyvinyl pyrolidone-vinyl acetate copolymer (PVP/VA copolymer) have a good compatibility with peroxide as well as a good solubility in water and ethanol. Accordingly, with using these polymers in the patch, the peroxide can be stabilized only by adjusting ratio of water to ethanol to be 9:1 to 0:10 without a stabilizer for peroxide. It is believed that the peroxide becomes compatible and thereby stabilized by formation of complex of polyvinyl pyrrolidone and peroxide via hydrogen bonding. Also, peroxides are found to be compatible with polymers having quaternary ammonium structure, such as polyquaternium.

According to the present invention, a mixture of water and ethanol is used as a solvent. Glass polymers, which are well compatible with peroxides typically, have so great hydrophilic property that they do not coat uniformly a surface of a release liner or other sheet. Using solvent mixture of water and ethanol can solve such problem so as to obtain a uniform sheet phase.

Therefore, the third aspect of the present invention relates a patch for tooth whitening comprising a peroxide as a tooth whitening agent, a glass polymer having a good compatibility with the peroxide, wherein the patch is stabilized at a high temperature by adjusting the ratio of water and ethanol without addition of a stabilizer for peroxide.

Also, the patch of the present invention further comprises a plasticizer to provide a sufficient flexibility for the patch. Suitable plasticizer includes propylene glycol, glycerin, and polyethylene glycol although it will vary depending on type of the polymer used and its composition.

Further, the present invention may include a polyphosphate as a whitening aid agent other than a peroxide as a main whitening agent in order to enhance a whitening effect.

For example, polyphosphate which can be used according to the present invention includes one or more selected from a group consisting of tetrasodium pyrophosphate (TSPP), sodium acid pyrophosphate (SAPP), sodium hexametaphosphate (SHMP), sodium tripolyphosphate (STP), sodium potassium tripolyphosphate (SKTP), tetrapotassium pyrophosphate (TKPP), ultraphosphates such as acidic sodium metapolyphosphate and acidic sodium polyphosphate. In general, it is known that the polyphosphate may be used effectively as a tartar controller in toothpaste to inhibit a formation of tartar or to remove tartar. Also, the polyphosphate is known to contribute to enhancing a tooth whitening effect since it can effectively remove stains formed on a surface of teeth, specially those formed of metal such as iron, calcium, magnesium, etc. from foods or working circumstances. The polyphosphate may act as a chelating agent to the above metal. Therefore, it is also expected according to the present invention that the polyphosphate used along with peroxide may provide inhibition of tartar formation and removal of tartar for a lengthened period of time. In practice, it is observed that when attaching the patch according to the present invention to teeth, surface of teeth or gaps between teeth get cleaned.

Polymers which can be used in the backing layer of the matrix type patch in accordance with the present invention includes for example, polyvinyl acetate, ethyl cellulose, poly methyl methacrylate, methacrylic copolymer, such as methacryloyl ethyl betain/methacrylates copolymer, commercially available under trade name Yukaformer from Mitsubishi, methacrylic acid copolymer, such as Eudragit L 100, Eudragit L 12,5, Eudragit L 100-55, Eudragit L 30D-55, aminoalkyl methacrylate copolymers, such as Eudragit E 100, Eudragit E 12,5, Eudragit RL 100, Eudragit RL 30D), cellulose acetate phthalate, Shellac or mixtures thereof. In addition, enteric coating polymers, which are not dissolved at pH 6 to 8 in an oral cavity condition, may be used as polymers in the backing layer.

In accordance with the present invention, it is possible to use any plasticizer in the backing layer for the same reason in the adhesive layer. In this case, other than propylene glycol, glycerin, and polyethylene can be used depending on the used solvent used, For example, caster oil, hydrogenated caster oil may be included.

Further, in order to make teeth look more whitened visually, any white pigment may be used in the backing layer. For example, titanium dioxide, talc, hydroxy apatite, zinc oxide, etc. may be used alone or in any mixture thereof. When these pigments are not compatible with a whitening agent in the adhesive layer, the surface-treated titanium dioxide may be used. In addition, it is possible to employ pearl material or a pigment of various colors depending on individuality.

In accordance with the present invention, substances such as enzyme, particularly dextranase, glucose oxidase that cannot be used in the conventional toothpaste due to the stability with time may be used alone or in a mixture. It is also possible to add papain, which is known to have a tooth whitening effect. Further, when applying the present invention for treatment of oral disease, triclosan, chlorohexidin, vitamin E or its derivatives, in particular vitamin E acetate, oxidant, chlorophyll or its derivatives which is effective to inhibit bad breath or flavors may be added.

BEST MODE FOR CARRYING OUT THE INVENTION

PREPARATION EXAMPLES

Example 1–10, Comparative Example 1–5

In accordance with the composition described below, patches of respective Examples 1–10 and Comparative Examples 1–5 are prepared. Abbreviations used below have following meanings.
TKPP: tetrapotassium pyrophosphate
SAPP: sodium acid pyrophosphate
TSPP: tetrasodium pyrophosphate

Example 1

| Adhesive preparation solution | |
| --- | --- |
| Polyvinyl alcohol | 10% |
| Polyvinyl pyrrolidone | 3% |
| Tetrasodium pyrophosphate peroxidate | 5% |
| Alkyl sulphate (SLS) | 2% |
| Glycerin | 3% |
| Water | to 100% |
| Backing preparation solution | |
| Ethyl cellulose | 8% |
| Eudragit | 5% |
| Caster oil | 4% |
| Ethanol | to 100% |

Example 2

| Adhesive preparation solution | |
| --- | --- |
| Polyvinyl pyrrolidone | 10% |
| Hydrogen peroxide | 5% |
| Glycerin | 10% |
| Ethanol | 30% |
| Water | to 100% |
| Backing preparation solution | |
| Polyvinyl acetate | 5% |
| Yukaformer (Mitsubishi) | 5% |
| Glycerin | 6% |
| Ethanol | to 100% |

Example 3

| Adhesive preparation solution | |
| --- | --- |
| Polyquaternium-39 | 10% |
| Carbamide peroxide | 10% |
| Ethanol | 50% |
| Water | to 100% |
| Backing preparation solution | |
| Cellulose acetate phthalate | 30% |
| Caster oil | 4% |
| Mixture of acetone and ethanol (acetone:ethanol = 4:1) | to 100% |

Example 4

| Adhesive preparation solution | |
| --- | --- |
| Polyalkyl vinyl ether-maleic acid copolymer (Gantrez S 97) | 12% |
| Tetrasodium pyrophosphate peroxidate | 6% |
| Span 85 | 2% |
| EDTA2Na | 0.2% |
| Water | to 100% |
| Backing preparation solution | |
| Ethyl cellulose | 10% |
| Caster oil | 6% |
| Ethanol | to 100% |

Example 5

| Adhesive preparation solution | |
| --- | --- |
| Polyalkyl vinyl ether-maleic acid copolymer (Gantrez S 97) | 12% |
| Tetrasodium pyrophosphate peroxidate | 6% |
| Alkyl sulphate (SLS) | 10% |
| NaOH | appropriate (pH up to 7) |
| Water | to 100% |
| Backing preparation solution | |
| Ethyl cellulose | 10% |
| Caster oil | 6% |
| Ethanol | to 100% |

Example 6

| Adhesive preparation solution | |
|---|---|
| Polyalkyl vinyl ether-maleic acid copolymer (Gantrez S 97) | 11% |
| Polyvinyl pyrrolidone | 3% |
| Hydrogen peroxide | 3% |
| SAPP | 4% |
| Alkyl ary sulphonate | 2% |
| NaOH | appropriate (pH up to 7) |
| Water | to 100% |
| Backing preparation solution | |
| Polymethyl methacrylate | 8% |
| Acetone | to 100% |

Example 7

| Adhesive preparation solution | |
|---|---|
| Polyquaternium-11 | 20% |
| Sodium percarbonate (PC) | 4% |
| TKPP | 4% |
| Alkyl diphenyl oxide disulphonate | 2% |
| Water | to 100% |
| Backing preparation solution | |
| Eudragit | 15% |
| Propylene glycol | 5% |
| Ethanol | to 100% |

Example 8

| Adhesive preparation solution | |
|---|---|
| Polyvinyl pyrrolidone | 10% |
| Hydrogen peroxide | 1.5% |
| SAPP | 2% |
| Alkyl diphenyl oxide disulphonate | 1% |
| Glycerin | 5% |
| Water | to 100% |
| Backing preparation solution | |
| Ethyl cellulose | 12% |
| Caster oil | 6% |
| Ethanol | to 100% |

Example 9

| Adhesive preparation solution | |
|---|---|
| Polyvinyl alcohol | 12% |
| Hydrogen peroxide | 1.5% |
| TSPP | 3.4% |
| Span 60 | 5% |
| Propylene glycol | 3% |
| Water | to 100% |
| Backing preparation solution | |
| Ethyl cellulose | 8% |
| Cellulose acetate phthalate | 2% |

-continued

| | |
|---|---|
| Mixture of acetone and ethanol (acetone:ethanol = 4:1) | to 100% |

Example 10

| Adhesive preparation solution | |
|---|---|
| Polyvinyl pyrrolidone | 18% |
| Hydrogen peroxide | 1.5% |
| Ethanol | to 100% |
| Backing preparation solution | |
| Ethyl cellulose | 10% |
| Eudragit | 2% |
| Caster oil | 7% |
| Ethanol | to 100% |

Comparative Example 1

| Adhesive preparation solution | |
|---|---|
| Polyvinyl alcohol | 10% |
| PEG-ascorbic acid | 6% |
| Propylene glycol | 3.1% |
| Water | to 100 |
| Backing preparation solution | |
| Ethyl cellulose | 10% |
| Caster oil | 4% |
| Ethanol | to 100 |

Comparative Example 2

| Adhesive preparation solution | |
|---|---|
| Polyalkyl vinyl ether-maleic acid copolymer (Gantrez S 97) | 12% |
| Tetrasodium pyrophosphate peroxidate | 6% |
| Dequest | 0.1% |
| Water | to 100 |
| Backing preparation solution | |
| Polyvinyl acetate | 5% |
| Yukaformer | 5% |
| Glycerin | 6% |
| Ethanol | to 100 |

Comparative Example 3

| Adhesive preparation solution | |
|---|---|
| Polyalkyl vinyl ether-maleic acid copolymer (Gantrez S 97) | 12% |
| Tetrasodium pyrophosphate peroxidate | 6% |
| EDTA | 0.15% |
| NaOH | appropriate (pH up to 7) |
| Water | to 100 |

-continued

Backing preparation solution

| | |
|---|---|
| Ethyl cellulose | 10% |
| Caster oil | 6% |
| Ethanol | to 100 |

Comparative Example 4

Adhesive preparation solution

| | |
|---|---|
| Carbopol | 12% |
| Hydrogen peroxide | 4.5% |
| SAPP | 0.48% |
| Glycerin | 80% |
| Water | to 100 |

Backing layer

Polyethylene strip

Comparative Example 5

Adhesive preparation gel

| | |
|---|---|
| Polyvinyl alcohol | 10% |
| Ascorbic acid | 2% |
| Propylene glycol | 2% |
| Water | to 100 |

Backing preparation solution

| | |
|---|---|
| Ethyl cellulose | 10% |
| Caster oil | 6% |
| Ethanol | to 100 |

Test Examples

Test Example 1

After storing patches prepared to have composition as described above for one week at 40° C., the patches were measured for changes of surface condition. They are graded on the following criteria: ○, increased in stickiness or discolored; X, neither increased in stickiness nor discolored.

TABLE 1

| | Stickiness | discolorization |
|---|---|---|
| Example 1 | X | X |
| Example 2 | X | X |
| Example 3 | X | X |
| Example 5 | X | X |
| Example 7 | X | X |
| Example 8 | X | X |
| Example 9 | X | X |
| Example 10 | X | X |
| Comparative Example 1 | ○ | ○ |
| Comparative Example 5 | ○ | ○ |

As seen in Table 1, Examples wherein the hydrophilic glass polymers were used according to the present invention did not show increase in stickiness and changes of surface condition in initial state or after storing for one week at a temperature of 40° C. However, Comparative examples 1 and 5 wherein polyvinyl alcohol which is a hydrophilic glass polymer was used in the adhesive layer, and instead of a peroxide, ascorbic acid or a derivative thereof such as PEG-ascorbic acid was used as a whitening agent showed increase in stickiness and severe discoloration as time passed.

Test Example 2

Tooth whitening effect of patches was measured according to the following method.

(1) Preparation of Stained Hydroxy Apatite (HAP) Tablet Specimen

Hydroxy apatite powder was formed into a tablet by means of an IR press. The resulting tablet was sintered at a temperature of 1000° C., molded with epoxy resin and etched using a strong acid. Staining of the tablet specimen was effected by conducting a course wherein the specimen was dipped in TSB (trypticase soybroth) solution having tea, coffee, iron, mucin dissolved therein and dried. The course was repeated several times and continued for one week. After staining, the specimen was washed slightly with running water by a little brushing to remove light stains, which would be dissolved in or easily eliminated by water. Finally, the specimen was dried at room temperature.

(2) Evaluation of Tooth Whitening Effect

Initial brightness values, L (100 indicates white and 0 indicates black) of respective specimens were measured by means of chroma meter. Patches for tooth whitening prepared in the above Preparation Examples and Comparative Examples were attached to moistened specimens. The specimens having patches attached thereto were stored in a thermohygrostat set at a temperature of 37° C. and a humidity of 95%. After a prescribed time, the patches were removed from specimens. The removed specimens were washed with running water by brushing and dried at room temperature. Each of specimens was measured for L value. Difference of L values between before and after attaching patches, Δ L was calculated for each patch. The results are shown in Table 2.

TABLE 2

| | Δ L (1 hour) | Δ L (3 hours) |
|---|---|---|
| Example 1 | 33.45 ± 3.25 | 38.95 ± 5.31 |
| Example 6 | 34.55 ± 4.55 | 39.23 ± 3.77 |
| Example 8 | 32.38 ± 3.44 | 40.00 ± 3.88 |
| Example 9 | 37.10 ± 3.44 | 38.00 ± 3.88 |
| Example 10 | 14.73 ± 4.11 | 32.25 ± 3.33 |
| Comparative Example 1 | 7.05 ± 1.71 | 15.26 ± 2.37 |
| Comparative Example 4 | 14.55 ± 2.41 | 30.35 ± 3.24 |
| Comparative Example 5 | 17.98 ± 3.05 | 20.05 ± 2.99 |

As seen in Table 2, patches comprising a peroxide as a whitening agent were superior in tooth whitening effect, compared to patches comprising a ascorbic acid or derivatives thereof. Also, it was noted that patches comprising a peroxide in combination with a polyphosphate or an addition compound of peroxide and a pyrophosphate as a tooth whitening agent exhibits much more improved tooth whitening effect, compared to patches comprising peroxide only.

Test Example 3

The patches for tooth whitening prepared in accordance with the composition described in Preparation examples were evaluated for their stability at a 40° C. temperature with time according to the following methods.

(1) Evaluation of Peroxide Content in a Patch

A solvate mixture, which is capable of dissolving both, a backing layer and an adhesive layer of a patch, was taken in an Erlenmeyer flask. An appropriate amount of respective test patches weighed precisely, was put into the flask and dissolved completely in the solvate mixture. 5 ml of 6 N HCl was added to the flask and about 2 g of potassium iodide was then dissolved in the solvate. The flask was kept for 1 hour in a cold and dark place. Then, contents of peroxide in the respective patches were quantified by titration using 50 mM solution of sodium thiosulphate. The results are shown in Table 3.

TABLE 3

| Residual peroxide | Ex.3 | Ex.4 | Ex.5 | Ex.10 | Comp. Ex. 2 | Comp. Ex. 3 | Comp. Ex. 4 |
|---|---|---|---|---|---|---|---|
| 1 week | 96% | 100% | 96% | 100% | 80% | 86% | 96% |
| 2 week | 89% | 100% | 93% | 100% | 65% | 70% | 91% |
| 4 week | 85% | 95% | 91% | 100% | 50% | 61% | 84% |
| 6 week | 85% | 91% | 88% | 94% | 42% | 50% | 71% |
| 8 week | 80% | 90% | 86% | 90% | 16% | 30% | 65% |

As shown from the results of Examples 4 and 5 and Comparative Examples 2 and 3 in table 3, adding a stabilizer for peroxide effects favorably in the stability with time when other compositional components are same. However, in case of Example 3 and Comparative Example 10 which did not include a stabilizer for peroxide, since the used glass polymer and peroxide are well compatible with each other, the stability with time of peroxide at a high temperature could be good only by adjusting the ratio of water and ethanol in the adhesive layer during the producing process. Comparative Example 4 is to evaluate Crest Whitestrips, a novel wet type whitening agent produced by Procter and Gamble. It was observed that residual peroxide content in the patch was reduced rapidly after 4 weeks.

INDUSTRIAL APPLICABILITY

As apparent from the above description, the patch for tooth whitening according to the present invention has a superior tooth whitening effect. Further, the present patch is dry type using a hydrophilic glass polymer in an adhesive layer. Accordingly, only upon attaching the patch to teeth the glass polymer is hydrated to provide an adhesion while making the whitening agent released. Therefore, it is safe and efficient in using for a short time period. In addition, the patch of the present invention has a good stability of peroxide in the patch at a high temperature.

What is claimed is:

1. A dry type patch for tooth whitening comprising an adhesive layer on a backing layer, wherein the adhesive layer contains a peroxide as a tooth whitening agent and a peroxide-compatible hydrophilic glass polymer as a base polymer, whereby the adhesive layer provides a strong adhesion to teeth while releasing the tooth whitening agent when hydrated on the enamel layers of teeth;

wherein the peroxide is one or more selected from the group consisting of hydrogen peroxide, carbamide peroxide, calcium peroxide, sodium percarbonate, sodium perborate, and tetrasodium pyrophosphate peroxidate;

wherein the hydrophilic glass polymer used in the adhesive layer is one or more selected from the group consisting of polyalkylvinylether-maleic acid copolymer, polyvinyl alcohol, polyacrylic acid, Poloxamer 407, polyvinyl pyrrolidone-vinyl acetate copolymer, polyvinyl pyrrolidone, Polyquaterium-11, Polyquaterium-39, carbomer, hydroxypropylmethyl cellulose, hydroxyethyl cellulose, hydroxypropyl cellulose, gelatin, sodium alginate;

wherein the adhesive layer further comprises a stabilizer for peroxide selected from the group consisting of alkylaryl sulphonates, alkyl sulphates, alkyl carboxylates, alkyldiphenyloxide disulphonates, sorbitan stearate, sorbitan monooleate, sorbitan trioleate, and mixtures thereof;

wherein the backing layer comprises a polymer selected from the group consisting of cellulose acetate phthalate, Shellac, polyvinylacetate, ethyl cellulose, polymethylmethacrylate, methacryloylethyl betain/methacrylates copolymer, methacrylic acid copolymer, aminoalkylmethacrylate copolymers, and mixtures thereof.

2. The dry type patch for tooth whitening according to claim 1, wherein the patch further comprises polyphosphate in order to enhance a teeth whitening effect.

3. The dry type patch for tooth whitening according to claim 2, wherein the polyphosphate is selected from the group consisting of tetrasodium pyrophosphate, sodium acid pyrophosphate, sodium hexametaphosphate, sodium tripolyphosphate, sodium potassium tripolyphosphate, tetrapotassium pyrophosphate, acidic sodium metapolyphosphate and combinations thereof.

4. The dry type patch for tooth whitening according to claim 1, wherein the backing layer further comprises a pigment selected from the group consisting of titanium dioxide, surface treated titanium dioxide, zinc oxide, hydroxy apatite, talc, pearl, a pigment of various colon, and mixtures thereof.

* * * * *